United States Patent

Cordi et al.

Patent Number: 5,436,261
Date of Patent: Jul. 25, 1995

[54] BENZOSPIROALKENE HETEROCYCLIC COMPOUNDS

[75] Inventors: Alex Cordi, Suresnes; Jean-Michel Lacoste, Sevres; Michel Laubie, Vaucresson; Tony Verbeuren, Vernouillet; Jean-Jacques Descombes, Neuilly-Plaisance, all of France

[73] Assignee: Adir et Compagnie, Courbevoie, France

[21] Appl. No.: 276,918

[22] Filed: Jul. 19, 1994

[30] Foreign Application Priority Data

Jul. 20, 1993 [FR] France .................. 93 08861

[51] Int. Cl.[6] .............. C07D 235/02; C07D 491/107; C07D 495/10; A61K 31/415
[52] U.S. Cl. ..................... 514/393; 548/301.1
[58] Field of Search ............ 548/301.1; 514/393

[56] References Cited

U.S. PATENT DOCUMENTS 2,716,648  8/1955  Jules et al. ............... 260/309.5
3,532,744 10/1970  Fletcher et al. ............ 260/518

OTHER PUBLICATIONS

Sax, N. I., et al. *Hawley's Condensed Chemical Dictionary* (New York, Van Nostrand Reinhold, 1987) p. 657 (month of publication unknown).

*Primary Examiner*—Mukund J. Shah
*Assistant Examiner*—K. L. Wong
*Attorney, Agent, or Firm*—Gordon W. Hueschen

[57] ABSTRACT

Compounds of formula (I):

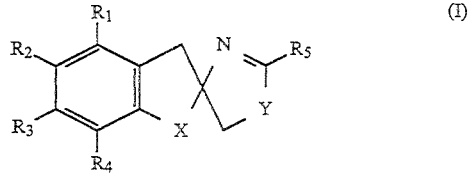

in which:
X represents —CH$_2$—, —(CH$_2$)$_2$—, —CH=CH—, —O—CH$_2$—, —S—CH$_2$—, —SO—CH$_2$— or —SO$_2$—CH$_2$—,
Y represents oxygen or sulfur or —NR$_6$—,
R$_1$ represents hydrogen or linear or branched (C$_1$–C$_6$) alkyl,
R$_2$ represents hydrogen or halogen, linear or branched (C$_1$–C$_6$) alkyl, (substituted or unsubstituted), hydroxyl, linear or branched (C$_1$–C$_6$) alkoxy or linear or branched (C$_1$–C$_6$) alkylthio,
R$_3$ represents hydrogen or halogen, linear or branched (C$_1$–C$_6$) alkyl (substituted or unsubstituted), hydroxyl, linear or branched (C$_1$–C$_6$) alkoxy or linear or branched (C$_1$–C$_6$)alkylthio,
R$_4$ represents hydrogen (on condition that, in this case, R$_1$ represents hydrogen), halogen, linear or branched (C$_1$–C$_6$) alkyl (substituted or unsubstituted) or hydroxyl, or alternatively
R$_1$ and R$_2$, R$_2$ and R$_3$, R$_3$ and R$_4$ or R$_4$ and X, together with the carbon atoms which bear them, form a benzene ring, on condition that, in the case where R$_1$ and R$_2$ form a benzene ring, X is other than —CH$_2$— or —(CH$_2$)$_2$—,
R$_5$ represents hydrogen or amino (substituted or unsubstituted),
R$_6$ has the same meaning as R$_1$, their isomers and also their. addition salts with a pharmaceutically acceptable acid and medicinal product containing the same are useful as partial $\alpha_1$ and $\alpha_2$ adrenergic agonist in the treatment of venous disease and migraine.

9 Claims, No Drawings

BENZOSPIROALKENE HETEROCYCLIC COMPOUNDS

The present invention relates to new benzospiroalkenes.

The adrenergic nervous system plays an important part at several levels, for example at arterial, venous, cardiac and renal level and in the central and peripheral autonomous nervous system. Products capable of interacting with adrenergic receptors can consequently induce a large number of physiological responses such as vasoconstriction, vasodilatation, increase or decrease in heart rate and variation of the force of contraction of cardiac muscle and of metabolic activities, as described by P. TIMMERMANS et al. in "Comprehensive Medicinal Chemistry" (Vol. III, p. 134°-185° C. HANSH Editor, Pergamon, Oxford). Different adrenergic compounds have been used in the past to modify these physiological responses or others.

Adrenergic stimulation in the peripheral nervous system is therapeutically useful when a vascular constriction takes place, such as in nasal, optic or ophthalmic congestion and in inflammation. An antagonist interaction can modulate the activity of the adrenergic neurons and hemodynamic equilibrium, and this is useful in numerous cardiovascular indications such as hypertension, and a variety of conditions of vascular spasm, as well as for remedying episodes of mild male impotence.

In the central nervous system, adrenergic stimulation is especially useful for inducing sedation and diuresis and in the treatment of hypertension and of addictive behavior. In contrast, an adrenergic antagonist can be useful in certain psychiatric or neurological disorders such as depression, as well as for the maintenance of cardiovascular equilibrium.

The compounds described in the present invention, apart from the fact that they are new, possess a profile of $\alpha_1$- and $\alpha_2$-adrenergic agonistic activities which makes them especially more capable of decreasing venous compliance without affecting arterial compliance, this effect being funhered by a rise in temperature. These very favorable properties indicate that the compounds of the invention are useful in the relief of symptoms of heavy legs associated with a deficiency of venous return, o especially in the lower limbs (venous disease). Furthermore, they can also be useful as sympathomimetics in the treatment of hypertension, anxiety, psychoses, diabetes, impotence and pain, and also as sedatives, vasoconstrictors, decongestants and ocular hypotensives and for remedying the symptoms of opiate abstinence. Lastly, the compounds of the invention are also capable of causing a fall in carotid blood flow rate, which also makes them useful in the treatment of migraine. This property has been shown, in particular, by R. SAXENA et at. (TIPS, Vol. 10, p. 200–204, 1989) and by M. O. den BOER et al. (Br. J. Pharmacol., 102, 323–330, 1991). The therapeutic value of the products of the invention is based on their selectivity for the subtypes of adrenergic receptors and their selective modulation of the adrenergic functions in different tissues and organs.

Partial α-adrenergic agonists have already been described in the literature. This applies, more especially, to the compounds described in Patent BE 687,657. However, the capacity of these compounds to decrease venous compliance without affecting arterial compliance is markedly less intense than that obtained with the compounds of the invention.

More specifically, the present invention relates to the compounds of formula (I):

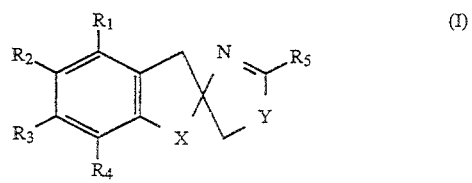

in which:

X represents —$CH_2$—, —$(CH_2)_2$—, —CH=CH—, —O—$CH_2$—, —S—$CH_2$—, —SO—$CH_2$— or —$SO_2$—$CH_2$—, Y represents an oxygen or sulfur atom or a group —$NR_6$—, $R_1$ represents a hydrogen atom or a linear or branched ($C_1$–$C_6$) alkyl group, $R_2$ represents a hydrogen or halogen atom, a linear or branched ($C_1$–$C_6$) alkyl group (unsubstituted or substituted with one or more halogen atoms), a hydroxyl group, a linear or branched ($C_1$–$C_6$) alkoxy group or a linear or branched ($C_1$–$C_6$) alkylthio group, $R_3$ represents a hydrogen or halogen atom, a linear or branched ($C_1$–$C_6$) alkyl group (unsubstituted or substituted with one or more halogen atoms), a hydroxyl group, a linear or branched ($C_1$–$C_6$) alkoxy group or a linear or branched ($C_1$–$C_6$) alkylthio group, $R_4$ represents a hydrogen atom (on condition that, in this case, $R_1$ represents a hydrogen atom), a halogen atom, a linear or branched ($C_1$–$C_6$) alkyl group (unsubstituted or substituted with one or more halogen atoms)or a hydroxyl group, or alternatively $R_1$ and $R_2$, $R_2$ and $R_3$, $R_3$ and $R_4$ or $R_4$ and X, together with the carbon atoms which bear them, form a benzene ring, on condition that, in the case where $R_1$ and $R_2$ form a benzene ring, X is other than —$CH_2$— or —$(CH_2)_2$—, $R_5$ represents a hydrogen atom or an amino group (unsubstituted or substituted with one or two linear or branched ($C_1$–$C_6$) alkyl groups), $R_6$ has the same meaning as $R_1$, their isomers and also their addition salts with a pharmaceutically acceptable acid.

Among pharmaceutically acceptable acids, hydrochloric, hydrobromic, sulfuric, phosphoric, acetic, lactic, malonic, succinic, fumaric, tartaric, maleic, citric, methanesulfonic, benzenesulfonic, and the like, acids may be mentioned without implied limitation.

Among the possible isomers of the compounds of formula (I), the enantiomers, the diastereoisomers, the epimers and also the tautomers may be mentioned.

The invention also encompasses the process for preparing the compounds of formula (I).

The compounds of formula (I) for which Y represents a group —$NR_6$ are obtained according to the process wherein a compound of formula (II):

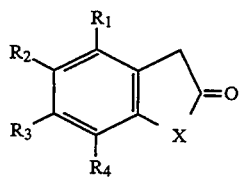

in which X, $R_1$, $R_2$, $R_3$ and $R_4$ have the same meaning as in the formula (I). is used as starting material, which is reacted: either with benzylamine in the presence of para-toluenesulfonic acid to yield the compound of formula (IH):

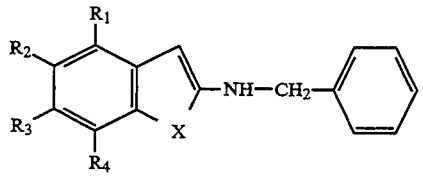

in which X, $R_1$, $R_2$, $R_3$ and $R_4$ have the same meaning as in the formula (I), which is reacted under an inert atmosphere with trimethylsilyl cyanide in the presence of zinc iodide to yield the compound of formula (IV):

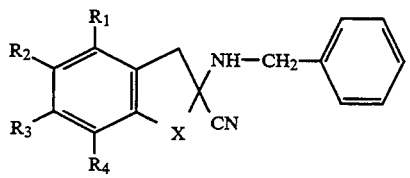

in which X, $R_1$, $R_2$, $R_3$ and $R_4$ have the same meaning as in the formula (I), which is reduced using lithium aluminum hydride and then by catalytic hydrogenation to yield the compound of formula (V):

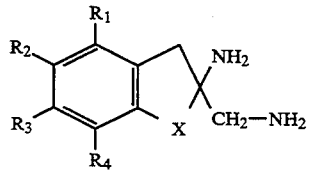

in which X, $R_1$, $R_2$, $R_3$ and $R_4$ have the same meaning as in the formula (I), or with potassium cyanide in the presence of ammonium chloride in an inert medium or with sodium cyanide in an acid medium, or alternatively with trimethylsilyl cyanide in the presence of zinc iodide and then with an alcoholic solution saturated with ammonia, to yield the compound of formula (VI):

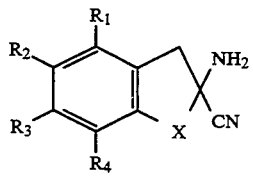

in which X, $R_1$, $R_2$, $R_3$ and $R_4$ have the same meaning as in the formula (I), which is reduced using lithium aluminum hydride to yield the compound of formula (V) described above, which compound of formula (V), is reacted with formamidine in an alcoholic medium or an alkylformate or with a cyanogen halide (followed, depending on the nature of the compound of formula (I) which it is desired to obtain, by an alkylation reaction using an alkyl halide), to yield the compound of formula (I/a), a special case of the compounds of the formula (I):

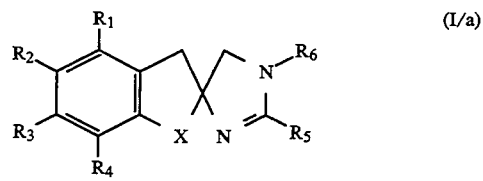

in which X, $R_1$, $R_2$, $R_3$, $R_4$, $R_5$ and $R_6$ have the same meaning as in the formula (I), which compound of formula (I/a), is purified, where appropriate, according to a standard purification technique, is subjected, if so desired, to a separation of its isomers according to a standard purification technique, and which are optionally converted to its addition salts with a pharmaceutically acceptable acid.

The compounds of formula (I) for which Y represents an oxygen or sulfur atom are obtained according to the process wherein a compound of formula (VI) described above is used as starting material, which is reacted with formic acid in an anhydrous medium saturated with hydrochloric acid, to yield the compound of formula (VII):

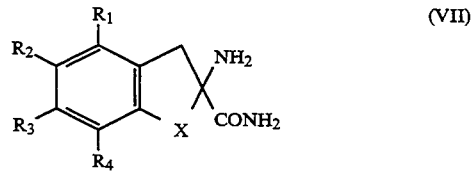

in which $R_1$, $R_2$, $R_3$, $R_4$ and X have the same meaning as in the formula (I), which is converted to the corresponding acid of formula (VIII) in a concentrated hydrochloric acid medium:

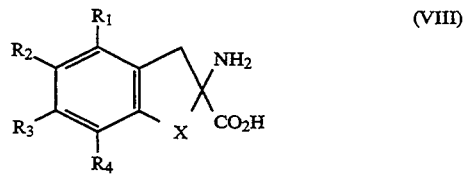

in which $R_1$, $R_2$, $R_3$, $R_4$ and X have the same meaning as in the formula (I), which undergoes a reduction with lithium aluminum hydride in an inert medium, to yield the compound of formula (IXa):

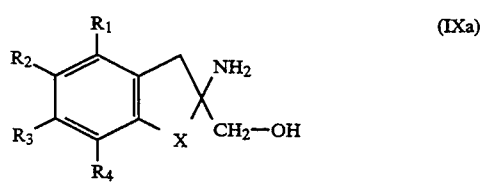

in which $R_1, R_2, R_3, R_4$ and X have the same meaning as in the formula (I), which compound (IXa) is convened, depending on the nature of the compounds of formula (I) which it is desired to obtain, to the corresponding tosylate using p-toluenesulfonic acid and is then reacted with thiourea or thioacetic acid, to yield, after hydrolysis, the compound of formula (IXb):

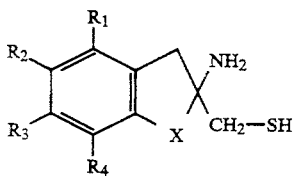

in which $R_1, R_2, R_3, R_4$ and X have the same meaning as in the formula (I), which compound of formula (IXa) or (IXb) is reacted with formamidine in an alcoholic medium or an alkylformate or with a cyanogen halide (followed, depending on the nature of the compound of formula (I) which it is desired to obtain, by an alkylation reaction using an alkyl halide), to yield the compound of formula (I/b), a special of the compounds of formula (I);

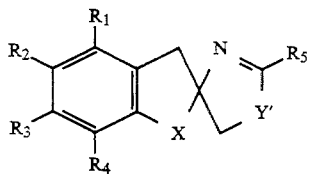

in which $R_1$, $R_2$, $R_3$, $R_4$, $R_5$ and X have the same meaning as above and Y' represents an oxygen or sulfur atom, which compound of formula (I/b) is purified, where appropriate, according to a standard purification technique, is subjected, if so desired, to a separation of its isomers according to a standard purification technique, and which are optionally converted to its addition salts with a pharmaceutically acceptable acid.

Compounds of formula (I), wherein $R_2, R_3$, or $R_4$ is a hydroxyl group, can be preferentially obtained by initially synthesizing the derivative of formula (I) possessing in $R_2$, $R_3$ or $R_4$ an alkoxy group, which is converted to the corresponding hydroxyl group by the action of boron tribromide in a dichloromethane medium.

The subject of the present invention is also pharmaceutical compositions containing as active principle at least one compound of general formula (I) or one of its addition salts with a pharmacologically acceptable acid, alone or in combination with one or more nontoxic, inert excipients or vehicles.

Among the pharmaceutical compositions according to the invention, there may be mentioned more especially those which are suitable for oral, parenteral or nasal administration, simple or sugar-coated tablets, sublingual tablets, hard gelatin capsules, troches, suppositories, creams, ointments, skin gels, and the like.

The dosage varies according to the patient's age and weight, the nature and severity of the complaint and also the administration route.

It can be oral, nasal, rectal or parenteral. Generally speaking, the unit dosage ranges between 0.1 and 1000 mg for a treatment administered in 1 to 3 doses per 24 hours.

The examples which follow illustrate the invention. The starting materials used are known products or are prepared according to known procedures.

EXAMPLE 1:

Spiro[(1,3-diaza-1-cyclopentene)-5,2'-(1',2',3',4'-tetrahydronaphthalene)]benzenesulfonate Stage A: 2-Benzylamino-3,4-dihydronaphthalene A mixture containing 171 mmol of-tetralone, 181 mmol of benzylamine and 100 mg of p-toluenesulfonic acid is brought to reflux with azeotropic distillation of the water/toluene mixture. After 2 hours of distillation, the medium is cooled and filtered. The expected product is obtained in the form of an oil after evaporation of the solvent.

Stage B: 2-Benzylamino-2-cyano-1,2,3,4-tetrahydronaphthalene 170 mmol of trimethylsilyl cyanide and 87 mmol of zinc iodide are added successively to a solution, maintained under nitrogen, containing 170 mmol of the compound obtained in the preceding stage in 600 ml of dichloromethane. The mixture is stirred at 20C. overnight and then washed with water.

After drying and evaporation of the organic phase, the expected product is obtained in the form of an oil.

Stage C: 2-Benzylamino-2-aminomethyl-1,2,3,4-tetrahydronaphthalene

A solution containing 152 mmol of the compound obtained in the preceding stage in 200 ml of anhydrous tetrahydrofuran is added dropwise to a suspension containing 290 mmol of lithium aluminum hydride in 700 ml of anhydrous tetrahydrofuran while the temperature is maintained below 30C. After 2 hours of stirring, the mixture is cooled to 0C and hydrolyzed by adding successively 11 ml o of water, 11 ml of 2N sodium hydroxide and 25 ml of water. The suspension is filtered and the tiltrate evaporated. The residue is dissolved in 400 ml of ethyl acetate. This phase is washed with water and extracted with 1N hydrochloric acid. The acidic aqueous phases are combined, alkalinized with 35% sodium hydroxide and extracted with ethyl acetate.

The organic phase is dried and evaporated to yield the expected product.

Stage D: 2-Amino-2-aminomethyl-1,2,3,4-tetrahydronaphthalene

A suspension containing 30 mmol of the compound obtained in the preceding stage, 125 mmol of ammonium formate, 6 g of palladium on charcoal (10%) and 250 ml of methanol is brought to reflux with stirring for 20 minutes. After cooling, filtration to remove the catalyst and evaporation of the solvent, the expected product is obtained in the form of an oil after purification by chromatography on a silica column using a dichloromethane/methanol/ammonia solution (90:10:1) as eluent.

Stage E: Spiro[(1,3-diaza-1-cyclopentene)-5,2'-(1',2',3',4'-tetrahydronaphthalene]benzenesulfonate A mixture containing 20 mmol of the compound obtained in the preceding stage and 20 mmol of formamidine acetate in 60 ml of ethanol is stirred at 20C under nitrogen for 12 hours. The solvent is evaporated off and the residue taken up with 50 ml of 1N hydrochloric acid.

The acid phase is washed with ethyl acetate and then alkalinized with 35% sodium hydroxide. The mixture is extracted with ethyl acetate. The combined organic phases are washed with aqueous sodium chloride solution and evaporated, and yield a solid residue. This residue is dissolved in 50 ml of ethanol and then treated with one equivalent of benzenesulfonic acid dissolved in 20 ml of ethanol.

The expected product is obtained after evaporation of the solvent and crystallization in an ethanoff ether mixture.

Melting point: 124C

| | Elemental microanalysis: | | | |
|---|---|---|---|---|
| | C % | H % | N % | S % |
| calculated | 62.77 | 5.85 | 8.13 | 9.31 |
| found | 63.06 | 6.03 | 8.23 | 9.52 |

Examples 2 to 12 were obtained according to the process described in Example 1, using the corresponding starting materials.

Example 2:

Spiro[(1,3-diaza-1-cyclopentene)-5,2'-(7'-trifiuoromethyl-1',2',3',4'-tetrahydronaphthalene)]fumarate Melting point: 168–170C.

| | Elemental microanalysis: | | |
|---|---|---|---|
| | C % | H % | N % |
| calculated | 55.14 | 4.63 | 7.56 |
| found | 55.02 | 4.63 | 7.68 |

Example 3:

Spiro[(1,3-diaza-1-cyciopentene)-5,2'-(6'-hydroxy-7'-methoxy-1',2',3',4'-tetrahydronaphthalene)]fumarate Melting point: 219–222C.

| | Elemental microanalysis: | | |
|---|---|---|---|
| | C % | H % | N % |
| calculated | 58.61 | 5.79 | 8.04 |
| found | 58.74 | 6.00 | 8.00 |

Example 4

Spiro[(1,3-diaza-1-cyclopentene)-5,2'-(5',7'-dimethyl-1',2',3',4'-tetrahydronaphthalene)]fumarate Melting point: 208–212C.

| | Elemental microanalysis: | | |
|---|---|---|---|
| | C % | H % | N % |
| calculated | 69.37 | 7.24 | 9.87 |
| found | 69.29 | 7.33 | 10.03 |

Example 5

Spiro[(1,3-diaza-1-cyclopentene)-5,2'-(6'-isopropyloxy-1',2',3,440 -tetrahydronaphthalene)]fumarate Melting point: 172–177C.

| | Elemental microanalysis: | | |
|---|---|---|---|
| | C % | H % | N % |
| calculated | 63.31 | 6.71 | 7.77 |
| found | 63.37 | 6.68 | 7.88 |

Example 6

Spiro[(1,3-diaza-1-cyclopentene)-5,2'-(5',7'-dimethoxy-1',2',3',4'-tetrahydronaphthalene)]fumarate Melting point: 150°154C.

| | Elemental microanalysis: | | |
|---|---|---|---|
| | C % | H % | N % |
| calculated | 59.66 | 6.12 | 7.73 |
| found | 59.38 | 5.87 | 7.80 |

Example 7

Spiro[(1,3-diaza-1-cyclopentene)-5,2'-(5',6'-dimethoxy-1',2',3',4'-tetrahydronaphthalene)]fumarate Melting point: 176–178C.

| | Elemental microanalysis: | | |
|---|---|---|---|
| | C % | H % | N % |
| calculated | 59.66 | 6.12 | 7.73 |
| found | 59.49 | 6.14 | 7.72 |

Example 8

Spiro[(1,3-diaza-1-cyclopentene)-5,2'-(6'-methyl-1',2',3',4'-tetrahydronaphthalene)]fumarate Melting point: 170°174C.

| | Elemental microanalysis: | | |
|---|---|---|---|
| | C % | H % | N % |
| calculated | 64.54 | 6.37 | 8.85 |
| found | 64.84 | 6.30 | 8.98 |

Example 9

Spiro[(1,3-diaza-1-cyciopentene)-5,2'-(5'-methoxy-7'-methyl-1',2',3',4'-tetrahydronaphthalene) ]fumarate Melting point: 178–181C.

| | Elemental microanalysis: | | |
|---|---|---|---|
| | C % | H % | N % |
| calculated | 62.48 | 6.33 | 7.95 |
| found | 62.42 | 6.40 | 8.09 |

Example 10

Spiro[(1,3-diaza-1-cyclopentene)-5,2'-(5'-trifluoromethylindan)]fumarate

Melting point: 175–177C.

| | Elemental microanalysis: | | |
|---|---|---|---|
| | C % | H % | N % |
| calculated | 53.94 | 4.24 | 13.42 |
| found | 53.71 | 4.07 | 13.50 |

Example 11

Spiro[(1,3-diaza-1-cyclopentene)-5,2'-(5'-methoxyindan)]fumarate

Melting point: 227–230C.

| Elemental microanalysis: | | | |
|---|---|---|---|
| | C % | H % | N % |
| calculated | 57.44 | 5.36 | 7.44 |
| found | 57.22 | 5.51 | 7.59 |

Example 12

Spiro[(1,3-diaza-1-cyclopentene)-5,3'-(7'-methoxychroman)]fumarate

Melting point: 186–190C.

| Elemental microanalysis: | | | |
|---|---|---|---|
| | C % | H % | N % |
| calculated | 57.48 | 5.43 | 8.38 |
| found | 57.60 | 5.27 | 8.41 |

Example 13

Spiro[(1,3-diaza-1-cyclopentene)-5,2'-(1',2',3',4'-tetrahydronaphthalene)]D(−)-tartrate, isomer α

The compound of Example I is resolved by means of L-dibenzoyltartaric acid by successive recrystallizations in ethanol. The enantiomeric purity is verified by chromatography on an $_1$-AGP chiral column using an $Na_2HPO_4$ aq. 0.01M/$NaH_2PO_4$ aq. 0.01M/n-propanol (60:40:1) mixture as eluent. The pure salt is then partitioned between IN sodium hydroxide and dichloromethane. The aqueous phase is extracted with dichloromethane. The organic phases are dried and evaporated. The solid residue is dissolved in ethanol, one equivalent of D(−)-tartaric acid is added and the mixture is brought to reflux. The expected product is obtained on cooling in the form of a white solid. Melting point: 185–186C.

| Elemental microanalysis: | | | |
|---|---|---|---|
| | C % | H % | N % |
| calculated | 57.14 | 5.99 | 8.33 |
| found | 57.08 | 5.74 | 8.22 |

Example 14

Spiro[(1,3-diaza-1-cyclopentene)-5,2'-(1',2',3',4'-tetrahydronaphthalene)]L(+)-tartrate, isomer β

The expected product is obtained according to the process described in Example 13, from the compound of Example 1 and L(+)-tartaric acid.

Example 15

Spiro[(1,3-diaza-1-cyclopentene)-5,2'-(6',7'-dichloro-1',2',3',4'-tetrahydronaphthalene)]fumarate Stage A: 2-Amino-2-cyano-7-chloro-1,2,3,4-tetrahydronaphthalene 141 mmol of potassium cyanide and 145 mmol of ammonium chloride are added successively to a vigorously stirred solution, maintained under nitrogen, containing 138 mmol of 7-chloroo3,4-dihydro-2(1H)-naphthalenone in 170 ml of methanol and 85 ml of water. After 48 hours of stirring at 20C., the mixture is concentrated. The residue is taken up with ethyl acetate. This organic phase is washed with water and then extracted with 1N hydrochloric acid. The acid phases are alkalinized with 35% sodium hydroxide and extracted with ethyl acetate. The organic phases are dried and evaporated and yield the expected product in the form of an oil.

Stage B: 2-Amino-2-aminomethyl-7-chloro-1,2,3,4-tetra-hydronaphthalene

A solution containing 76 mmol of the product obtained in the preceding stage in 100 ml of anhydrous tetrahydrofuran is added dropwise at a temperature below 20C. to a suspension containing 175 mmol of lithium aluminum hydride in ml of anhydrous tetrahydrofuran. After one hour of stirring, the mixture is cooled to 0C. and hydrolyzed by adding 6.5 ml of 2N sodium hydroxide and then ml of water. The resulting suspension is filtered and the flitrate evaporated. The residue is dissolved in ethyl acetate and this solution is washed with water and extracted with 1N hydrochloric acid.

The acid phases are then alkalinized with 35% sodium hydroxide and extracted with ethyl acetate.

After drying and evaporation, the expected product is obtained in the form of an oil.

Stage C:

Spiro[(1,3-diaza-1-cyclopentene)-5,2'-(6',7'-dichloro-1',2',3',4'-tetrahydronaphthalene)]fumarate A mixture containing 26 mmol of the compound obtained in the preceding stage and 29 mmol of form-amidine acetate in 100 ml of ethanol is stirred at 20C under a nitrogen atmosphere for 12 hours. After evaporation of the solvent, the residue is taken up with 1N hydrochloric acid. The acid phase is washed with ethyl acetate, alkalinized with 35% sodium hydroxide and extracted with ethyl acetate.

The combined organic phases are washed with saturated sodium chloride solution and then evaporated. The solid residue is taken up with ethanol treated with one equivalent of fumaric acid dissolved in 30 ml of ethanol.

After evaporation of the solvent, the expected product is obtained on recrystallization of the residue in ethanol.

Melting point: 138–140C.

| Elemental microanalysis: | | | | |
|---|---|---|---|---|
| | C % | H % | N % | Cl % |
| calculated | 57.06 | 5.09 | 8.32 | 10.53 |
| found | 57.15 | 5.18 | 8.31 | 10.43 |

Examples 16 to 28 were obtained according to the process described in Example 15, using the corresponding starting material.

Example 16

Spiro[(1,3-diaza-1-cyclopentene)-5,2'-(7'-methoxy-1',2',3',4'-tetrahydronaphthalene)]fumarate Melting point: 188–190C.

| Elemental microanalysis: | | | |
|---|---|---|---|
| | C % | H % | N % |
| calculated | 61.44 | 6.07 | 8.43 |
| found | 61.49 | 6.02 | 8.26 |

Example 17

Spiro[(1,3-diaza-1-cyclopentene)-5,2'-(5',7'-dichloro-1',2',3',4'-tetrahydronaphthalene)]fumarate Melting point: 204–205C.

| Elemental microanalysis: | | | | |
|---|---|---|---|---|
| | C % | H % | N % | Cl % |
| calculated | 51.77 | 4.34 | 7.55 | 19.10 |
| found | 51.84 | 4.34 | 7.62 | 18.80 |

Example 18

Spiro[(1,3-diaza-1-cyclopentene)-5,2'-(6',7'-dichloro-1',2',3',4'-tetrahydronaphthalene)]fumarate Melting point: 214°216C.

| Elemental microanalysis: | | | | |
|---|---|---|---|---|
| | C % | H % | N % | Cl % |
| calculated | 51.77 | 4.34 | 7.55 | 19.10 |
| found | 51.56 | 4.22 | 7.45 | 19.03 |

Example 19

Spiro[(1,3-diaza-1-cyclopentene)-5,2'-(6',7'-dimethoxy-1',2',3',4'-tetrahydronaphthalene)]fumarate Melting point: 138–140C.

| Elemental microanalysis: | | | |
|---|---|---|---|
| | C % | H % | N % |
| calculated | 59.66 | 6.12 | 7.77 |
| found | 59.20 | 6.07 | 7.58 |

Example 20

Spiro[(1,3-diaza-1-cyclopentene)-5,2'-(6'-chloro-1',2',3',4'-tetrahydronaphthalene)]fumarate Melting point: 201–203C.

| Elemental microanalysis: | | | | |
|---|---|---|---|---|
| | C % | H % | N % | Cl % |
| calculated | 57.06 | 5.09 | 8.32 | 10.53 |
| found | 57.12 | 4.86 | 8.20 | 10.47 |

Example 21

Spiro[(1,3-diaza-1-cyclopentene)-5,2'-(6'-methoxy-1',2',3',4'-tetrahydronaphthalene)]fumarate Melting point: 172–174C.

| Elemental microanalysis: | | | |
|---|---|---|---|
| | C % | H % | N % |
| calculated | 61.44 | 6.07 | 8.43 |
| found | 61.35 | 5.65 | 8.41 |

Example 22

Spiro[(1,3-diaza-1-cyclopentene)-5,2'-(5'-chloro-1',2',3',4'-tetrahydronaphthalene)]fumarate Melting point: 204–206C.

| Elemental microanalysis: | | | | |
|---|---|---|---|---|
| | C % | H % | N % | Cl % |
| calculated | 57.06 | 5.09 | 8.32 | 10.53 |
| found | 57.26 | 5.22 | 8.27 | 10.48 |

Example 23

Spiro[(1,3-diaza-1-cyclopentene)-5,2'-(7'-fluoro-1',2',3',4'-tetrahydronaphthalene)]fumarate Melting point: 196–200C.

| Elemental microanalysis: | | | |
|---|---|---|---|
| | C % | H % | N % |
| calculated | 63.15 | 5.67 | 10.23 |
| found | 63.16 | 5.65 | 10.20 |

Example 24

Spiro[(1,3-diaza-1-cyclopentene)-5,2'-(7'-methyl-1',2',3',4'-tetrahydronaphthalene)]fumarate Melting point: 210–214C.

| Elemental microanalysis: | | | |
|---|---|---|---|
| | C % | H % | N % |
| calculated | 68.53 | 6.87 | 10.38 |
| found | 69.02 | 6.88 | 10.75 |

Example 25

Spiro[(1,3-diaza-1-cyclopentene)-5,2'-(5',7'-difluoro-1',2',3',4'-tetrahydronaphthalene)]fumarate Melting point: 118°124C.

| Elemental microanalysis: | | | |
|---|---|---|---|
| | C % | H % | N % |
| calculated | 60.00 | 5.03 | 9.99 |
| found | 59.68 | 4.84 | 9.99 |

Example 26

Spiro[(1,3-diaza-1-cyclopentene)-5,3'-(chroman)]fumarate

Melting point: 175–176C.

| Elemental microanalysis: | | | |
|---|---|---|---|
| | C % | H % | N % |
| calculated | 59.20 | 5.31 | 9.21 |
| found | 58.79 | 5.45 | 8.16 |

Example 27

Spiro[(1,3-diaza-1-cyclopentene)-5,3'-(thiochroman)]fumarate

Melting point: 176–178C.

| Elemental microanalysis: | | | | |
|---|---|---|---|---|
| | C % | H % | N % | S % |
| calculated | 56.24 | 5.03 | 8.74 | 10.01 |

-continued

| | Elemental microanalysis: | | | |
|---|---|---|---|---|
| | C % | H % | N % | S % |
| found | 56.22 | 5.16 | 8.82 | 9.94 |

Example 28

Spiro[(1,3-diaza-1-cyciopentene)-5,2'-(indan)]hydrochloride

Melting point: 210C.

| | Elemental microanalysis: | | | |
|---|---|---|---|---|
| | C % | H % | N % | Cl % |
| calculated | 63.31 | 6.28 | 13.42 | 16.99 |
| found | 63.15 | 6.26 | 13.31 | 17.06 |

Example 29

Spiro[(1,3-diaza-1-cyclopentene)-5,2'-(6'-methoxy-1',2',3',4'-tetrahydronaphthalene)]fumarate hydrate, isomer α

The expected product was obtained by resolving the compound described in Example 21 by means of (R)-(−)-10-camphorsulfonic acid. The salt of the pure enantiomer thereby obtained was neutralized and then salified again using fumaric acid.

The enantiomeric purity was verified by liquid chromatography on a DIACEL-OD column using an isopropanol/n-heptane/diethylamine (25:75:0.08) mixture as eluent.

Melting point: 105–107C.

| | Elemental microanalysis: | | |
|---|---|---|---|
| | C % | H % | N % |
| calculated | 58.58 | 6.33 | 8.00 |
| found | 58.25 | 6.50 | 7.82 |

Example 30

Spiro[(1,3-diaza-1-cyclopentene)-5,2'-(6'-methoxy-1',2',3',4'-tetrahydronaphthalene)]fumarate hydrate, isomer β

The expected product was isolated according to the process described in Example 29 after resolving the compound of Example 21 with (S)-(+)-10-camphorsulfonic acid.

Melting point: 105–107C

| | Elemental microanalysis: | | |
|---|---|---|---|
| | C % | H % | N % |
| calculated | 58.28 | 6.33 | 8.00 |
| found | 57.83 | 6.38 | 7.87 |

Example 31

Spiro[(1,3-diaza-1-cyclopentene)-5,2'-(2,3'-dihydrophenalene)] ½ fumarate

Stage A: 2-Amino-2-cyano-2,3-dihydrophenalene 1 ml of concentrated hydrochloric acid is added dropwise to a vigorously stirred mixture of 13.7 mmol of 1,3-dihydro-2-phenalenone and 40 mmol of sodium cyanide in 60 ml of water and 80 ml of ethyl ether. After one hour of stirring at 20C., and when settling has taken place, the organic phase is separated, washed with water, dried and evaporated. The residue obtained is treated with 20 ml of a methanolic solution of ammonia (3.5M) with stirring for 5 hours at 20C.

After evaporation of the solvent, the residual oil is taken up with 30 ml of ethyl ether and extracted with 1N hydrochloric acid. The combined acid phases are alkalinized with 35% sodium hydroxide and then extracted with ether. After drying and evaporation, the expected product is obtained in the form of an oil.

Stage B: 2-Amino-2-aminomethyl-2,3-dihydrophenalene

The expected product is obtained according to the process described in Stage B of Example 15.

Stage C: Spiro[(1,3-diaza-1-cyclopentene)-5,2'-(2',3'-dihydrophenalene)] ½ fumarate The expected product is obtained according to the process described in Stage C of Example 15.

Melting point: 245–250C.

| | Elemental microanalysis: | | |
|---|---|---|---|
| | C % | H % | N % |
| calculated | 72.84 | 5.75 | 9.99 |
| found | 72.58 | 5.64 | 9.87 |

Examples 32 to 34 were obtained according to the process described in Example 31.

Example 32

Spiro[(1,3-diaza-1-cyclopentene)-5,2'-(5',8'-dimethyl-1',2',3',4'-tetrahydronaphthalene)]fumarate Melting point: 192–194C.

| | Elemental microanalysis: | | |
|---|---|---|---|
| | C % | H % | N % |
| calculated | 65.44 | 6.71 | 8.48 |
| found | 65.29 | 6.60 | 8.45 |

Example 33

Spiro[(1,3-diaza-1-cyciopentene)-5,3'-(5',6'-benzochroman)]fumarate

Melting point: 200–204C.

| | Elemental microanalysis: | | |
|---|---|---|---|
| | C % | H % | N % |
| calculated | 64.40 | 5.12 | 7.91 |
| found | 64.72 | 5.34 | 8.13 |

Example 34

Spiro[(1,3-diaza-1-cyclopentene)-5,3'-(7',8'-benzochroman)]fumarate

Melting point: 185–190C.

| | Elemental microanalysis: | | |
|---|---|---|---|
| | C % | H % | N % |
| calculated | 64.40 | 5.12 | 7.91 |
| found | 63.80 | 5.20 | 8.07 |

Example 35

Spiro[(1-oxa-2-amino-3-aza-2-cyclopentene)-4,2'-(1',2',3',4'-tetrahydronaphthalene)]hydrochloride Stage A: 2-Amino-2-cyano-1,2,3,4-tetrahydronaphthalene hydrochloride 34.2 mmol of -tetralone and 40 mmol of trimethylsilyl cyanide are stirred at room temperature. 25 mg of zinc iodide are then added to the above mixture. After 30 minutes of stirring, 50 ml of a saturated methanolic solution of ammonia are added and the mixture is left overnight with stirring at room temperature.

After evaporation of the solvent, the residual oil is dissolved in 500 ml of ether, dried and then treated with 5 ml of ethereal hydrogen chloride. The expected product is obtained on filtering off the solid formed.

Stage B: 2-Amino-2-aminocarbonyl-1,2,3,4-tetrahydronaphthalene hydrochloride

A solution containing 25.4 mmol of the compound obtained in the preceding stage in 80 ml of formic acid is cooled to 0C and saturated with anhydrous hydrogen chloride.

After the evolution of gas has ceased, the solvent is evaporated off and the residue taken up with 50 ml of acetone. The expected product is obtained on o filtering off the white solid which crystallizes.

Stage C: 2-Amino-1,2,3,4-tetrahydro-2-naphthalenecarboxylic acid

A suspension containing 21.8 mmol of the compound obtained in the preceding stage in 25 ml of 6N hydrochloric acid is brought to reflux until with isopropanol and concentrated again. The solid obtained is dissolved in water and the pH is taken to 7 by adding 1N sodium hydroxide. The expected product is the white solid formed, which is filtered off and dried.

Stage D: 2-Amino-2-hydroxymethyl-1,2,3,4-tetrahydronaphthalene

A suspension containing 40 mmol of lithium aluminum hydride in 100 ml of tetrahydrofuran is added dropwise under a nitrogen atmosphere at room temperature to a solution containing 20 mmol of the compound obtained in the preceding stage in 50 ml of anhydrous tetrahydrofuran. The mixture is brought to reflux for one hour.

Alter cooling to 0C, 1.5 ml of water, 1.5 ml of 2.5N sodium hydroxide and 3 ml of water are added successively. The mixture is stirred and the white solid which forms is filtered off and washed with tetrahydro-furan. The flitrates are combined and evaporated and yield the expected product in the form of an oil.

Stage E: Spiro[(1-oxa-2-amino-3-aza-2-cyclopentene)-4,2'-(1',2',3',4'-tetrahydronaphthalene)]hydrochloride A solution containing 12mmol of cyanogen bromide in 5 ml of dichloromethane is added rapidly at 0C to a solution containing 10.6 mmol of the product obtained in the preceding stage in 20 ml of dichloromethane.

The mixture is stirred overnight at room temperature and the solid formed is filtered off and washed with dichloromethane. The combined tiltrates are washed with potassium bicarbonate solution, dried and evaporated.

The expected product is obtained after purification of the residue by chromatography on a silica column using dichloromethane, a dichloromethane/ethanol (98:2) mixture and lastly a dichloromethane/ethanol/ammonia solution (95:4.5:0.5) mixture as eluent. The oil obtained is dissolved in ether and treated with ethereal hydrogen chloride. The precipitate is then filtered off and recrystallized in an isopropanol/ether mixture.

Melting point: 206C.

| | Elemental microanalysis: | | | |
|---|---|---|---|---|
| | C % | H % | N % | Cl% |
| calculated | 60.38 | 6.33 | 11.73 | 14.85 |
| found | 59.97 | 6.17 | 10.96 | 14.72 |

Example 36

Spiro[(1,3-diaza-2-amino-1-cyclopentene)-5,2'-(1',2',3',4'-tetrahydronaphthalene)]hydrobromide 6.3 mmol of cyanogen bromide in 5 ml of dichloromethane are added at 0C to 5.7 mmol of 2-amino-2-amino-methyl-1,2,3,4-tetrahydronaphthalene (obtained in Stage D of Example 1) dissolved in 50 ml of dichloromethane. The solution is stirred overnight at room temperature. The expected product which forms is filtered off and recrystallized in isopropanol.

Melting point: 209C

| | Elemental microanalysis: | | | |
|---|---|---|---|---|
| | C % | H % | N % | Br % |
| calculated | 51.08 | 5.72 | 14.89 | 28.32 |
| found | 51.12 | 5.80 | 14.59 | 28.00 |

Example 37

Spiro[(1-oxa-3-aza-2-cyclopentene)-4,2'-(1',2',3',4'-tetrahydronaphthalene)]

Stage A: 2-Formamido-2-hydroxymethyl-1,2,3,4-tetrahydronaphthalene

A solution containing 5.6 mmol of the compound obtained in Stage D of Example 35 in 5 ml of ethyl formate is left overnight at room temperature. The solution is then diluted with 25 ml of dichloromethane, the solid is filtered off and the tiltrate is evaporated. The residue is then purified by chromatography on a silica column using a dichloromethane/ethanol (95:5) mixture as eluent.

Stage B:

Spiro[(1-oxa-3-aza-2-cyclopentene)-4,2'-(1',2',3',4'-tetrahydronaphthalene)]

A solution containing 7.5 mmol of diethylamino-sulfur trifluoride in 3 ml of dichloromethane is added dropwise at −10C under a nitrogen atmosphere to a solution containing 3.5 mmol of the compound obtained in the preceding stage in 40 ml of dichloromethane.

After 2 hours of stirring at −10C, 25 ml of 25% ammonia solution are added to the above mixture. The organic phase is separated after settling has taken place, filtered, dried and evaporated. The solid residue is purified on a silica column using a dichloromethane/ethanol (99:1) mixture as eluent. The expected product is then distilled at 125C under reduced pressure (p=30 mmHg) and thereafter recrystallized in heptane at −30C.

| | Elemental microanalysis: | | |
|---|---|---|---|
| | C % | H % | N % |
| calculated | 76.98 | 7.00 | 7.48 |
| found | 76.83 | 7.42 | 7.58 |

Examples 38 to 43 were obtained according to the process described in Example 1, using the corresponding starting materials.

Example 38

Spiro[(1,3-diaza-1-cyclopentene)-5,2'-(7'-isopropyl-(1',2',3',4'-tetrahydronaphthalene)]3/2 fumarate Melting point: 192–194C

| Elemental microanalysis: | | | |
|---|---|---|---|
| | C % | H % | N % |
| calculated | 62.67 | 6.51 | 6.96 |
| found | 62.60 | 6.59 | 7.02 |

Example 39

Spiro[(1,3-diaza-1-cyclopentene)-5,2'-(7'-tert-butyl-(1',2',3',4'-tetrahydronaphthalene)]fumarate Melting point: 188–190C

| Elemental microanalysis: | | | |
|---|---|---|---|
| | C % | H % | N % |
| calculated | 67.02 | 7.31 | 7.82 |
| found | 66.70 | 7.43 | 7.80 |

Example 40

Spiro[(1,3-diaza-1-cyclopentene)-5,2'-(7'-ethyl-(1',2',3',4'-tetrahydronaphthalene)]fumarate Melting point: 148–152C

| Elemental microanalysis: | | | |
|---|---|---|---|
| | C % | H % | N % |
| calculated | 65.44 | 6.71 | 8.48 |
| found | 65.63 | 6.84 | 8.47 |

Example 41

Spiro[(1,3-diaza-1-cyclopentene)-5,2'-(6',7'-dimethyl-(1',2',3',4'-tetrahydronaphthalene)]fumarate Melting point: 189–192C

| Elemental microanalysis: | | | |
|---|---|---|---|
| | C % | H % | N % |
| calculated | 65.44 | 6.71 | 8.48 |
| found | 64.80 | 6.61 | 8.46 |

Example 42

Spiro[(1,3-diaza-1-cyclopentene)-5,2'-(1',2',3',4',6',7',8'-heptahydrocyclopenta[g]naphthalene)]hemifumarate of formula:

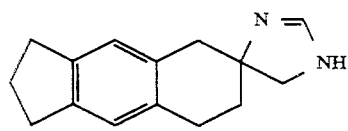

Melting point: 205–209C

| Elemental microanalysis: | | | |
|---|---|---|---|
| | C % | H % | N % |
| calculated | 71.81 | 7.09 | 9.85 |
| found | 71.40 | 6.99 | 9.49 |

Example 43

Spiro[(1,3-diaza-1-cyclopentene)-5,2'-(5',6'-dimethylindan)]fumarate

Melting point: 214–216C

| Elemental microanalysis: | | | |
|---|---|---|---|
| | C % | H % | N % |
| calculated | 64.54 | 6.37 | 8.85 |
| found | 64.16 | 6.34 | 8.66 |

Example 44

Spiro[(1,3-diaza-1-cyclopentene)-5,2'-(6'-isopropyloxy-1',2',3',4'-tetrahydronaphthalene)]fumarate, isomer α

The expected product is obtained by resolving the compound of Example 5 by means of di(para-toluoyl)-D-tartaric acid by successive recrystallizations in ethanol. The enantiomeric purity is verified by chiral chromatography on a DIACEL-OJ column using an isopropanol-heptane/diethylamine (10:90:0.1) mixture as eluent. The salt is then partitioned between 1N sodium hydroxide and dichloromethane. After extraction with dichloromethane, the organic phases are dried and evaporated. The residue is then dissolved in ethanol with one equivalent of fumaric acid and the mixture is brought to reflux. The expected product is then obtained after cooling in the form of a white solid.

Melting point: 175–177C

| Elemental microanalysis: | | | |
|---|---|---|---|
| | C % | H % | N % |
| calculated | 63.32 | 6.71 | 7.77 |
| found | 62.91 | 6.59 | 7.73 |

Example 45

Spiro[(1,3-diaza-1-cyclopentene)-5,2'-(6'-isopropyloxy-1',2',3',4'-tetrahydronaphthalene)]fumarate, isomer β

The expected product is obtained according to the process described in Example 44, using di(para-toluoyl)-L-tartaric acid for the resolution.

Melting point: 175–177C

| Elemental microanalysis: | | | |
|---|---|---|---|
| | C % | H % | N % |
| calculated | 63.32 | 6.71 | 7.77 |
| found | 63.08 | 6.77 | 7.67 |

Example 46

(S)-Spiro[(1,3-diaza-1-cyclopentene)-5,2'-(7'-methyl-1',2',3',4'-tetrahydronaphthalene)]fumarate Stage A: (S)-2-[(R)-Methylbenzylamino]-2-cyano-1,2,3,4-tetrahydronaphthalene 13 mmol of (R)-(+)-α-methylbenzylamine hydrochloride (of enantiomeric purity greater than 99%) and then 19 mmol of sodium cyanide are added successively to a solution, maintained under nitrogen, of 20mmol of 7-methyl-2-tetralone in a mixture containing 13 ml of ethanol, 3.2 ml of methanol and 3 ml of water. The mixture is stirred for 20 hours at 20C. The precipitate formed is then filtered off, washed with ice-cold ethanol and dried, and yields the expected product.

Stage B: (S)-2-[(R)-Methylbenzylamino]-2-aminomethyl-1,2,3,4-tetrahydro naphthalene A solution containing 15 mmol of the compound obtained in the preceding stage in 30 ml of ether is added dropwise to a suspension containing 35 mmol of lithium aluminum hydride in 60 ml of anhydrous ether while the temperature is maintained at 30C. After 2 hours of stirring, the mixture is cooled to 5C and hydrolyzed with 1.3 ml of water, 1.50 ml of 2N sodium hydroxide and 2.5 ml of water. After filtration, the flitrate is evaporated. The residue is dissolved in 50 ml of ethyl acetate. This phase is washed with water and then extracted with 1N hydrochloric acid. The acidic aqueous phases are alkalinized with 35% sodium hydroxide and extracted with ethyl acetate. The expected product is obtained after drying and evaporation of the organic phases.

Stage C: (S)-2-Amino-2-aminomethyl-1,2,3,4-tetrahydro-naphthalene

A solution containing 10 mmol of the compound obtained in the preceding stage in 40 ml of methanol and 3.5 ml of acetic acid is hydrogenated at atmospheric pressure in the presence of 500 mg of palladium dihydroxide for 20 hours. After the catalyst has been filtered off, the tiltrate is evaporated and the residue is dissolved in 40 ml of ethyl acetate. This phase is washed with water and extracted with 1N hydrochloric acid. The acid phases are alkalinized with 35% sodium hydroxide and extracted with dichloromethane. The organic phases are dried and evaporated and yield the expected product in the form of a colorless oil.

Stage D: (S)-Spiro[(1,3-diaza-1-cyclopentene)-5,2'-(7'-methyl-1',2',3',4'-tetrahydronaphthalene)]fumarate A mixture containing 8 mmol of the compound obtained in the preceding stage and 8 mmol of formamidine acetate in 30 ml of ethanol is stirred at 20C under a nitrogen atmosphere for 12 hours. The solvent is evaporated off and the residue is taken up with 20 ml of 1N hydrochloric acid. This phase is washed with ethyl acetate and then alkalinized with 35% sodium hydroxide. After extraction with ethyl acetate, the organic phases are washed with aqueous sodium chloride solution and then evaporated. The residue is then dissolved in 15 ml of ethanol and thereafter treated with one equivalent of fumaric acid in 10 ml of ethanol. The expected product is then obtained after evaporation of the solvent and crystallization in an ethanol/ether mixture. The enantiomeric purity is verified by chiral chromatography on a DIACEL-OJ column using an isopropanol/n-heptane/ diethylamine (60:1000:0.8) mixture as eluent. The absolute configuration was determined by X-ray diffraction on a monocristal of the compound.

Melting point: 162–164C

| | Elemental microanalysis: | | |
|---|---|---|---|
| | C % | H % | N % |
| calculated | 64.54 | 6.37 | 8.85 |
| found | 64.19 | 6.29 | 8.87 |

Example 47

(R)-Spiro[(1,3-diaza-1-cyclopentene)-5,2'-(7'-methyl-1',2',3',4'-tetrahydronaphthalene)]fumarate The expected product is obtained according to the process described in Example 46, using (S)-(−)-ct-methyl-benzylamine in Stage A.

Melting point: 162–164C

| | Elemental microanalysis: | | |
|---|---|---|---|
| | C % | H % | N % |
| calculated | 64.54 | 6.37 | 8.85 |
| found | 64.54 | 6.33 | 8.79 |

Pharmacological study ,of the compounds of the invention

Example 48

In vitro study on dog femorai arteries and saphenous veins

The technique used is based on that described by FOWLER et al., (J. Pharmacol. Exp. Ther., 229, 712–718, 1984). Male or female mongrel dogs weighing approximately 15–25 kg were used as a source of organs. The animals are anesthetized with pentobarbital (30 mg/kg intravenously). The legs are incised and the vessels removed. They are placed in Krebs-Ringer fluid (118 mM NaCl; 25 mM NaHCO$_3$; 10mM glucose; 4.7 mM KCl; 1.25 mM CaCl$_2$; 1.19 mM MgSO$_4$; 1.14 mM KH$_2$PO$_4$) at room temperature and a stream of carbogen (95% O$_2$, 5% CO$_2$) is bubbled through. The fat is then carefully removed from these vessels, which are thereafter cut into rings 2 mm wide and mounted under a baseline tension of 4 g (femoral arteries) or 1 g (saphenous veins) in tanks thermostated at 37C containing Krebs-Ringer fluid with a stream of carbogen constantly bubbled through. A lower hook constitutes the fixed point, while the upper hook is connected to an isometric force gauge. The variations in tension are digitized, stored on disk and processed by a computer system. After mounting, the organs are left undisturbed for 90 minutes, rinsing being performed every 30 min. After readjustment of the baseline tension, a contraction is induced with a single dose of KCl (100 mM). After stabilization, washing and return to the baseline, a contraction is induced by a single dose of phenylephrine (submaximal concentrations) in order to regularize the following contractions. After washing and return to the baseline, an effect/concentration curve is plotted by adding cumulative doses of agonist (the spacing between the doses is on a semilogarithmic scale). This experiment enables the 50% effective concentration (EC$_{50}$) to be calculated in the following manner: the tension values are first converted to percentages relative to the maximum effect produced by 100 mM KCl. This EC$_{50}$ is determined by nonlinear regression by the SIMPLEX method (M. S. CACECI, Byte, 340–362, 1984), calculated according to the L. MICHAELIS and M. L. MENTEN model of the law of mass action (Biochem. Zeitschrift, 49, 333–369, 1913). E=(Emax*C$^n$-

)($EC^n + C^n$) with E=effects; Emax=maximum effect; C=concentration; EC=$EC_{50}$; n=HILL's number The products of the invention contract dog arteries and veins. The maximum extent of these contractions is smaller than that obtained with KCl. The results obtained are presented in the table below:

| | ARTERY | | VEIN | |
|---|---|---|---|---|
| Example | $EC_{50}$ (μM) | Max (% KCl) | $EC_{50}$ (μM) | Max (% KCl) |
| 1 | 5.9 | 19 | 1.3 | 98 |
| 8 | 13 | 12 | 2.1 | 44 |
| 9 | 0.8 | 60 | 3.9 | 81 |
| 17 | 24 | 10 | 1.9 | 44 |
| 24 | 70 | 8 | 0.16 | 57 |
| 31 | 0.5 | 10 | 1.6 | 44 |
| 46 | 15 | 36 | 1.86 | 48 |

Example 49

In vivo study in PITBED RATS

Male Sprague-Dawley rats (300–400 g) are anesthetized with ether. The trachea is canulated, the spinal cord is destroyed by means of a steel rod and the animal is immediately placed under artificial respiration. The vagal nerves are sectioned. The carotid arteries are ligated; a catheter is placed in one and is used to record blood pressure. A further three catheters are placed in the jugular veins and the veins of the penis and are used for injections. The animals'temperature is maintained at 36° C. The animal is pretreated by an injection of tertatolol (100 g/kg). The animal is also pretreated 10 minutes later with prazosin (100 g/kg) or yohimbine (1 mg/kg) when it is desired to determine the alpha$_1$—or alpha$_2$-adrenergic properties of the product. Ten minutes later, increasing cumulative doses of the product are injected every 20 seconds. Variations in blood pressure are detected using a Statham P23XL pressure cell and are recorded. The pressure values are expressed in mmHg. This experiment enables the concentration that increases the pressure by 20 mm Hg ($C_{20}$) to be calculated by non-linear regression according to the Michaelis and Menten model of the law of mass action, as described above. The maximum effect obtained is then converted to a percentage relative to the maximum effect produced by phenylephrine. The alpha$_1$- or alpha$_2$-adrenergic components of the product are assessed by means of the ratio of the $C_{20}$ values obtained in the presence of prazosin or yohimbine to the values obtained in the absence of these antagonists. In pithed rats, the products of the invention produce prazosin- and yohimbine-sensitive hypertension. The results are collated in the table below:

| | $C_{20}$ (μg/kg) | Ratio $C_{20}$ treated/$C_{20}$ control | |
|---|---|---|---|
| Example | Control | Prazosin | Yohimbine |
| 1 | 4 | 1.9 | 4.7 |
| 3 | 0.9 | 9.2 | 2.9 |
| 5 | 68 | 11 | 66 |
| 7 | 137 | 2.9 | 2.4 |
| 24 | 30 | 1.4 | 1.5 |
| 46 | 6.8 | 3.7 | 3.4 |

Example 50

In vivo study of carotid blood flow in anesthetized dogs

Dogs (12-18kg) are anesthetized with pentobarbital (30mg/kg i.v.). Anesthesia is then maintained by a perfusion of 0.8 ml/h of 6% pentobarbital. The animals are placed under assisted respiration and their temperature is maintained at 37C (Harvard thermostated blanket). Blood pressure and heart rate are measured by means of a Millar probe in the femoral artery or brachial artery, via a transducer and a Gould biotach. The blood flow in the carotid arteries is recorded by means of a Gould SP2202 electromagnetic flow meter.

In this model, the anti-migraine product sumatriptan at a dose of 300 g/kg i.v. produces a fall in carotid blood flow of 47 6% (n=5). The compound of Example 46 of the present invention, at a dose of 5 g/kg i.v., produces a fall in carotid blood flow of 62±4% (n−6).

Example 51

Pharmaceutical composition

| Preparation formula for 1000 tablets containing a 10 mg dose | |
|---|---|
| Compound of Example 1 | 10 g |
| Hydroxypropylcellulose | 2 g |
| Wheat starch | 10 g |
| Lactose | 100 g |
| Magnesium stearate | 3 g |
| Talc | 3 g |

We claim:

1. A compound of formula (I):

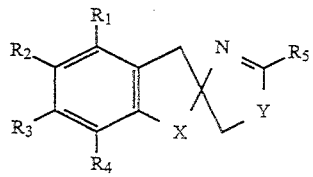

in which

X represents —CH$_2$—, —(CH$_2$)$_2$—, —CH=CH—, —O—CH$_2$—, —S—CH$_2$—, —SO—CH$_2$— or —SO$_2$—CH$_2$—, Y represents —NR$_6$—, R$_1$ represents hydrogen or linear or branched (C$_1$-C$_6$) alkyl, R$_2$ represents hydrogen, linear or branched (C$_1$-C$_6$) alkyl which is unsubstituted or substituted with one or more halogen, hydroxyl, linear or branched (C$_1$-C$_6$) alkoxy or linear or branched (C$_1$-C$_6$) alkylthio, R$_3$ represents hydrogen, halogen, linear or branched (C$_1$-C$_6$) alkyl which is unsubstituted or substituted with one or more halogen, hydroxyl, linear or branched (C$_1$-C$_6$) alkoxy, or linear or branched (C$_1$-C$_6$) alkylthio, R$_4$ represents hydrogen on condition that, in this case, R$_1$ represents hydrogen, halogen, linear or branched (C$_1$-C$_6$) alkyl which is unsubstituted or substituted with one or more halogen, or hydroxyl, or alternatively R$_1$ and R$_2$, R$_2$ and R$_3$, R$_3$ and R$_4$, or R$_4$ and X, together with the carbon atoms which bear them, form a benzene ring, on condition that, in the case where R$_1$ and R$_2$ form a benzene ring, X is other than —CH$_2$— or —(CH$_2$)$_2$—, R₅ represents hydrogen or amino which is unsubstituted or substituted with one or two linear or branched ($C_1$–$C_6$) alkyl, and R₆ has the same meaning as R₁, its optical isomers and also its addition salts with a pharmaceutically acceptable acid.

2. A compound of claim 1 selected from those in which X represents —(CH₂)₂—, its optical isomers, and also its addition salts with a pharmaceutically-acceptable acid.

3. A compound of claim 1 selected from those in which Y represents —NH—, its optical isomers, and also its addition salts with a pharmaceutically-acceptable acid.

4. A compound of claim 1 selected from those wherein R₁ represents hydrogen, its optical isomers and also its addition salts with a pharmaceutically-acceptable acid.

5. A compound of claim 1 selected from those wherein R₅ represents hydrogen, its optical isomers, and also its addition salts with a pharmaceutically-acceptable acid.

6. A compound of claim 1 which is selected from spiro[(1,3-diaza-1-cyclopentene)-5,2'-(1',2',3',4'-tetrahydronaphthalene)], its isomers and also its addition salts with a pharmaceutically-acceptable acid.

7. A compound of claim 1 which is selected from spiro[(1,3-diaza-1-cyclopentene)-5,2'-(7'-methyl-1',2',3',4'-tetrahydronaphthalene)], its optical isomers, and also its addition salts with a pharmaceutically-acceptable acid.

8. A method for treating a mammal afflicted with a condition requiring partial α₁ and α₂ adrenergic agonist for the treatment of venous disease and migraine, comprising the step of administering to the mammal an amount of a compound of claim 1 which is effective for alleviation of said condition.

9. A pharmaceutical composition useful in the treatment of venous disease or migraine, comprising as active principle an effective amount of a compound of claim 1 which is effective for said treatment, together with a pharmaceutically-acceptable excipient or vehicle.

* * * * *

UNITED STATES PATENT AND TRADEMARK OFFICE
CERTIFICATE OF CORRECTION

PATENT NO. : 5,436,261
DATED : July 25, 1995
INVENTOR(S) : Alex Cordi, Jean-Michel Lacoste, Michel Laubie, Tony Verbeuren, Jean-Jacques Descombes.

It is certified that error appears in the above-indentified patent and that said Letters Patent is hereby corrected as shown below:

TITLE PAGE, ITEM [57], Column 2, line 29; "their. addition" should read -- their addition --
Column 1, line 9; "level" should read -- levels --
Column 1, line 17; "p. 134°-185° C. HANSH" should read -- p. 134-185 C.HANSH --
Column 2, line 17; delete "-SO-" at the end of the line.
Column 2, line 18; insert -- -SO -- to the beginning of the line, to make it read -- $-SO_2-CH_2-$, --
Column 3, line 14; "(IH):" should read -- (III): --
Column 6, line 36; "11 ml o of" should read -- 11 ml of --
Column 6, line 38; "tiltrate" should read -- filtrate --
Column 7, line 5; "ethanoff ether" should read -- ethanol/ether --
Column 7, line 33; "cyciopentene" should read -- cyclopentene --
Column 7, line 59; "1',2', 3',440-" should read -- 1',2',3',4'- --
Column 8, line 41; "cyciopentene" should read -- cyclopentene --
Column 9, line 24; "I" shoud read -- 1 --
Column 9, line 30; "IN" should read -- 1N --
Column 9, line 62; "7-chloroo3" should read -- 7-chloro-3 --
Column 10, line 11; "in ml" should read -- in 250 ml --
Column 10, line 14; "then ml" should read -- then 14 ml --
Column 11, line 28; "cyciopentene)" should read -- cyclopentene) --
Column 13, line 9; "cyciopentene)" should read -- cyclopentene) --
Column 13, line 31; "propanolJn-" should read -- propanol/n- --
Column 15, line 25; "on o filtering" should read -- on filtering --

UNITED STATES PATENT AND TRADEMARK OFFICE
CERTIFICATE OF CORRECTION

PATENT NO. : 5,436,261
DATED : July 25, 1995
INVENTOR(S) : Alex Cordi, Jean-Michel Lacoste, Michel Laubie, Tony Verbeuren, Jean-Jacques Descombes.

It is certified that error appears in the above-indentified patent and that said Letters Patent is hereby corrected as shown below:

Column 15, line 31; insert the following lines after "until". -- dissolution is complete.  The solvent is evaporated off and the residue is taken up --

Column 15, line 37; "dronaphthaiene" should read -- dronaphthalene --

Column 17, line 32; "cyciopentene)-" should read -- cyclopentene --

Column 18, line 30; "propanol-heptane/" should read -- propanol/n-heptane/ --

Column 18, line 49; "isopropyioxy-" should read -- isopropyloxy- --

Column 18, line 67; delete the space between "tetrahy" and "dronaphthalene"

Column 19, line 34; "tiltrate" should read -- filtrate --

Column 20, line 13; "(S)-(-)-ct-" should read -- (S)-(-)-a- --

Column 20, line 27; "femorai" should read -- femoral --

Column 22, line 16; "(n-6)." should read -- (n=6). --

Column 22, line 48; insert the word "halogen," between the words "hydrogen," and "linear"

Column 22, line 51; insert a comma"," after the word "alkoxy"

UNITED STATES PATENT AND TRADEMARK OFFICE
CERTIFICATE OF CORRECTION

PATENT NO. : 5,436,261
DATED : July 25, 1995
INVENTOR(S) : Alex Cordi, Jean-Michel Lacoste, Michel Laubie, Tony Verbeuren, Jean-Jacques Descombes.

It is certified that error appears in the above-indentified patent and that said Letters Patent is hereby corrected as shown below:

Column 23, line 6; insert a hyphen "-" between the words "pharmaceutically" and "acceptable"

Column 23, line 16; insert a comma "," after the word "isomers"

Column 24, line 3; insert "optical" before the word "isomers" also insert a comma "," after the word "isomers"

Signed and Sealed this

Seventeenth Day of October, 1995

Attest:

BRUCE LEHMAN

*Attesting Officer*     *Commissioner of Patents and Trademarks*